United States Patent
Gurin et al.

(10) Patent No.: US 10,682,327 B2
(45) Date of Patent: Jun. 16, 2020

(54) PREPARED FOODS HAVING HIGH EFFICACY OMEGA-6/OMEGA-3 BALANCED POLYUNSATURATED FATTY ACIDS

(71) Applicant: Omega Foods, LLC, Two Rivers, WI (US)

(72) Inventors: Michael H. Gurin, Glenview, IL (US); Andrew G. Konopacki, Denmark, WI (US)

(73) Assignee: Omega Foods, LLC, Two Rivers, WI (US)

( * ) Notice: Subject to any disclaimer, the term of this patent is extended or adjusted under 35 U.S.C. 154(b) by 773 days.

(21) Appl. No.: 14/055,619

(22) Filed: Oct. 16, 2013

(65) Prior Publication Data

US 2014/0106047 A1    Apr. 17, 2014

Related U.S. Application Data

(63) Continuation of application No. PCT/US2012/033973, filed on Apr. 17, 2012.

(60) Provisional application No. 61/632,827, filed on Apr. 17, 2011.

(51) Int. Cl.
| | |
|---|---|
| *A61K 31/202* | (2006.01) |
| *C11B 5/00* | (2006.01) |
| *A23D 7/01* | (2006.01) |
| *A23D 7/005* | (2006.01) |
| *A23D 7/00* | (2006.01) |
| *A23L 25/10* | (2016.01) |
| *A23L 27/60* | (2016.01) |
| *A23L 33/115* | (2016.01) |
| *A23D 9/06* | (2006.01) |
| *A61K 47/22* | (2006.01) |

(52) U.S. Cl.
CPC ............ *A61K 31/202* (2013.01); *A23D 7/003* (2013.01); *A23D 7/0053* (2013.01); *A23D 7/011* (2013.01); *A23D 9/06* (2013.01); *A23L 25/10* (2016.08); *A23L 27/60* (2016.08); *A23L 33/115* (2016.08); *A61K 47/22* (2013.01); *C11B 5/0035* (2013.01); *C11B 5/0071* (2013.01); *A23V 2002/00* (2013.01)

(58) Field of Classification Search
CPC . A23L 1/3006; A23L 1/38; A23L 1/24; A23L 27/60; A23L 33/115; A23D 7/003; A23D 7/0053; A23D 7/011; A23D 7/00; A23D 9/00; A23D 9/007; A61K 8/06; A61K 31/202; A61K 47/22; A61K 47/24; A23V 2002/00

USPC ......................................... 426/541, 542, 601
See application file for complete search history.

(56) References Cited

U.S. PATENT DOCUMENTS

| | | | |
|---|---|---|---|
| 5,922,704 A | 7/1999 | Bland | ........................... 514/185 |
| 2004/0052920 A1* | 3/2004 | Koike | ...................... A21D 2/16 |
| | | | 426/601 |
| 2005/0002992 A1* | 1/2005 | McCleary | ............ A61K 31/198 |
| | | | 424/439 |
| 2005/0054724 A1 | 3/2005 | Mustad et al. | ................ 514/547 |
| 2005/0244564 A1 | 11/2005 | Perlman | ....................... 426/602 |
| 2007/0196560 A1* | 8/2007 | Ayoub | .................... A23L 25/10 |
| | | | 426/633 |
| 2007/0248738 A1 | 10/2007 | Abril et al. | .................... 426/601 |

FOREIGN PATENT DOCUMENTS

| | | | | |
|---|---|---|---|---|
| FR | 2909839 A1 * | 6/2008 | ............... | A23D 9/00 |
| WO | WO 2005/020698 | 3/2005 | ............... | A23D 9/00 |

OTHER PUBLICATIONS

"Mechanism Study of Chitosan on Lipid Metabolism in Hyperlipidemic Rats" to Guang-Fei Xu, hereinafter chitosan 1, Asia Pacific Journal of Clinical Nutrition 16 S1 (Apr. 1, 2007) p. 313-317, 1 page abstract.*
KitoZyme launches vegetal chitosan ingredient, Apr. 16, 2010 3 pages.*
"Best Food Choices for Omega 3 and Omega 6 and Omega 9 Essential Fatty Acids" obtained from http://www.dailyperricone.com/2008/12/best-food-choices-for-omega-3-and-omega-6-and-omega-9, Dec. 3, 2008; 4 pages.*
Choe et al., Mechanisms of Antioxidants in the Oxidation of Foods; Comprehensive Reviews in Food Science and Food Safety—vol. 8, 2009—pp. 345-358. (Year: 2009).*
International Search Report issued in a corresponding foreign application, pp: 1-3 (dated Nov. 29, 2012).
Written Opinion issued in a corresponding foreign application, pp: 1-3 (dated Nov. 29, 2012).
International Preliminary Report on Patentability issued in a corresponding foreign application, pp: 1-5 (dated Oct. 31, 2013).
European Extended Search Report issued in a corresponding foreign application, pp: 1-6 (dated Oct. 6, 2014).

* cited by examiner

*Primary Examiner* — Jyoti Chawla
(74) *Attorney, Agent, or Firm* — J. Peter Paredes; David G. Rosenbaum; Rosenbaum IP, P.C.

(57) ABSTRACT

A composition and method for supplementing food, nutrition, and diet systems with omega-6 to omega-3 balanced oils comprising a synergistic blend of at least two oils. The composition further comprises a synergistic blend of long chain omega-3 oil as a means to further increase the nutritional value. The composition provides an effective increase in therapeutic and pharmacological properties in nutrition and diet systems.

19 Claims, 3 Drawing Sheets

Table 1 - Master batch in grams, except as noted otherwise

| Example / Ingredients | 2nd Oil e.g., High Oleic Oil Plenish | Fish Oil 50% | Fish Oil 20% | Medium Chain Triglycerides | Egg Yolk Phospholipids | Inositol (ppm) |
|---|---|---|---|---|---|---|
| MB-1 | 100 | 100 | 0 | 100 | 100 | 100 |
| MB-2 | 20 | 100 | 0 | 50 | 100 | 100 |
| MB-3 | 0 | 100 | 0 | 100 | 100 | 100 |
| MB-4 | 100 | 100 | 0 | 20 | 100 | 50 |
| MB-5 | 20 | 100 | 0 | 20 | 120 | 100 |
| MB-6 | 20 | 0 | 60 | 80 | 80 | 60 |
| MB-7 | 100 | 50 | 0 | 0 | 100 | 0 |

FIG. 1

Table 2 - Master batch Plus in ppm, except as noted

| Example/Additives | Coffee Fruit | Vitamin E (mixed trienols) | Sulforaphane Glucosinolate | Curcumin C3 Complex | Manganese Oxide |
|---|---|---|---|---|---|
| AD-1 | 100 | 100 | 0 | 0 | 0 |
| AD-2 | 100 | 100 | 0 | 0 | 20 |
| AD-3 | 0 | 100 | 0 | 0 | 0 |
| AD-4 | 0 | 100 | 0 | 0 | 20 |
| AD-5 | 0 | 100 | 0 | 0 | 100 |
| AD-6 | 0 | 400 | 0 | 0 | 50 |
| AD-7 | 0 | 400 | 100 | 0 | 0 |
| AD-8 | 0 | 200 | 200 | 0 | 0 |
| AD-9 | 0 | 200 | 0 | 100 | 20 |
| AD-10 | 100 | 400 | 0 | 0 | 50 |
| AD-11 | 100 | 400 | 100 | 0 | 20 |
| AD-12 | 0 | 400 | 100 | 100 | 20 |

FIG. 2

Table 3 - Finished Consumer Product

| Food product in grams | Second Oil, e.g., High Oleic Oil Plenish | Master batch for OCLC mg per serving | Additive for 100 ppm on oil weight fraction | Pineapple Juice for g per serving | Medium Chain Triglycerides for g per serving |
|---|---|---|---|---|---|
| Milk | 0 | any | any | 0 | 2 |
| Juice | 0 | any | any | 20 | 0 |
| Mayonnaise | balance of oil | any | any | 0 | 0 |
| Salad Dressing | balance of oil | any | any | 5 | 0 |
| Milk | balance for 2% | any | any | 0 | 0 |
| Juice | 0 | any | any | 200 | 0 |
| Mayonnaise | balance of oil | any | any | 0 | 0 |
| Salad Dressing | balance of oil | any | any | 0 | 0 |
| Milk | balance for 4% | any | any | 0 | 2 |
| Juice | 0 | any | any | 0 | 2 |
| Mayonnaise | balance of oil | any | any | 3 | 5 |
| Salad Dressing | balance of oil | any | any | 3 | 5 |

PREPARED FOODS HAVING HIGH EFFICACY OMEGA-6/OMEGA-3 BALANCED POLYUNSATURATED FATTY ACIDS

CROSS REFERENCE TO RELATED APPLICATIONS

This application is a continuation and claims priority under 35 U.S.C. § 120 and § 365(c) to PCT International Application PCT/US2012/033973, with an international filing date of Apr. 17, 2012 which claims priority to U.S. application Ser. No. 13/088,417 filed on Apr. 17, 2011 and U.S. Provisional Application Ser. No. 61/632,827 with a filing date of Apr. 17, 2011 all of which are incorporated by reference in their entireties.

FIELD OF THE INVENTION

The present invention relates generally to the fields of food science and functional foods, more particularly to delivery formulations relating to nutraceuticals, pharmaceuticals, foods, and functional foods.

BACKGROUND OF THE INVENTION

Dietary fish oil preparations containing omega-3 polyunsaturated fatty acids have been reported to have a number of health-inducing characteristics. As asserted in various publications, dietary fish oil preparations are believed to promote more healthful levels of triglyceride, HDL cholesterol, homocysteine, and blood pressure as well as enhance the effectiveness of statin drugs used to treat cholesterol levels. See, e.g., U.S. Pat. Nos. 3,082,228, 4,097,602, and 5,698,594; British Patent 2,197,199; and International Patent Publication WO 87/02247.

Fatty acids come in various categories of carbon chain length, meaning the number of carbon atoms in the aliphatic tail that are linked together per molecule. The "aliphatic tail" is composed of a series of carbon atoms, as noted, from the terminal methyl group (i.e., $-CH_3$) to the carboxyl group ($-COOH$) at the other end of the fatty acid; the carbon of the carboxyl group is not included in the considered number of carbons of the aliphatic chain.

Short chain fatty acids have fewer than six carbon atoms in their aliphatic tails, such as alpha-linolenic acid ("ALA"). Medium chain fatty acids have between six and 12 carbon atoms. And long chain fatty acids have greater than 12 carbons, such as docosahexaenoic acid ("DHA") and eicosapentaenoic acid ("EPA").

Fatty acids can be "saturated," meaning that each carbon atom of the aliphatic tail is linked by C—C single bonds, the lowest energy state of carbon-to-carbon bonds that are most difficult to digest. "Unsaturated" fatty acids, however, include at least one double bond between adjacent carbon atoms of the aliphatic tail, which affords more energy to such bonds and renders the unsaturated fatty acid more readily digested; as suggested by the prefix, "polyunsaturated" fatty acids have multiple double-bonds and are generally known to be more healthful.

Some fatty acids found in nature are "essential" in that humans cannot manufacture them and therefore must ingest them because they are needed for certain cellular functions. Notable among the essential polyunsaturated fatty acids are the omega-3 category and the omega-6 category, so-named for the position of a first double bond after the third carbon or the sixth carbon from the methyl terminal.

Omega-3 fatty acids are believed to be the primary source of the above-mentioned good effects of dietary fish oil preparations. Such omega-3 fatty acids are found naturally in the oil of cold-water fish, such as mackerel, salmon, sardines, anchovies and tuna; omega-3 fatty acids are also found naturally in extracted alpha-linolenic acid oil from plants, such as flaxseed and canola (rapeseed). However, it is the case that omega-6 fatty acids are far more plentiful in the most readily available sources of oil that is part of the human diet, namely vegetable oil extracted from any of various commercially raised oil seeds, e.g., corn, soy, canola, flax. The ratios of omega-6 to omega-3 fatty acids in some common vegetable oils are: canola 2:1, soybean 7:1, olive 3-13:1, sunflower (no omega-3), flax 1:3, cottonseed (almost no omega-3), peanut (no omega-3), grapeseed oil (almost no omega-3) and corn oil 46:1 ratio of omega-6 to omega-3.

Currently, western diets generally contain a ratio of omega-6 to omega-3 fatty acids of more than 15:1. This change in fatty acid consumption toward excessive intakes of omega-6 polyunsaturated fatty acids resulting in a very high omega-6 to omega-3 ratio has been implicated as the source of or a contributor to a variety of diseases, including cardiovascular, cancer, inflammatory, and autoimmune diseases.

There is a growing body of scientific evidence indicating the health benefits of a lower omega-6 to omega-3 fatty acid ratio, including improved immune function as well as cardiovascular, bone, and mental health benefits. In particular, studies suggest that an omega-6 to omega-3 ratio of less than 6:1 may be associated with health benefits, whereas a ratio of 10:1 or greater may be associated with adverse health effects. Various federal agencies and scientific organizations are placing an increased emphasis on increasing omega-3 fats in the diet.

The present invention attempts to solve the problems caused by an imbalance of healthful fatty acids in the modern diet, as well as others.

SUMMARY

It is an object of the present invention to maximize the bioavailability and serving size of omega-3 long chain polyunsaturated fatty acids ("PUFAs") by preparing an omega-3 PUFA delivery system that minimizes adverse enzymatic and oxidation reactions from manufacturing to consumption of the delivery system and during consumption of the delivery system.

The omega-6/omega-3 balanced polyunsaturated fatty acid blend ("Omega-6:3 PUFA Blend") comprises an oil blend that can be used in the preparation of base compositions for various foods, nutraceuticals, functional foods, pharmaceuticals, etc.

One particular, exemplary embodiment is the use of the Omega-6:3 PUFA Blend in an enhanced food, generically referred to as a "functional food," such as a mayonnaise or a sauce enhanced by the Omega 6:3 PUFA Blend. The Omega-6:3 PUFA Blend retains oxidation resistance and stability once incorporated into a base composition, in contrast to known blends.

As utilized in the present application, the Omega-6:3 PUFA Blend maintains an omega-6 to omega-3 ratio of about 4:1 or better (meaning that the omega-6 component occupies a lesser amount of the omega-6 to omega-3 ratio, such as about 3:1, about 2:1, about 1:1, etc.), a ratio of short chain omega-3 PUFAs to long chain omega-3 PUFAs from about 5:1 or better (meaning that the short chain omega-3 component occupies a lesser amount of said ratio, such as about 4:1, about 3:1, about 2:1, etc.), and deliver at least about 50 mg of combined DHA and/or EPA per standard serving of the base composition into which the Omega-6:3 PUFA Blend is incorporated.

The Omega-6:3 PUFA Blend can also include various additives to help improve oxidation resistance and stability. These additives may include antioxidants, phytosterols, and the like.

Examples of prepared foods manufactured using a base composition utilizing the Omega-6:3 PUFA Blend include, but are not limited to: mayonnaise or mayonnaise-like foods, salad dressing or salad dressing-like foods, French dressing or French dressing-like foods, peanut butter or peanut butter-like foods, nut butter, pasta sauce, alfredo sauce, and the like.

As used herein, long chain omega-3 PUFAs means DHA or EPA. DHA is docosahexaenoic acid 22:6(n-3), and EPA is eicosapentaenoic acid 20:5(n-3).

As used herein, short chain omega-3 PUFAs means ALA. ALA is alpha-linolenic acid, 18:3 (n-3).

As used herein, medium chain triglycerides ("MCTs") are medium chain (6 to 12 carbons) fatty acid esters of glycerol.

As used herein, functional food means a modified food that claims to improve health or well-being by providing benefit beyond that of the traditional nutrients it contains. As noted above, a functional food can be enhanced in its health-improving or -promoting characteristics by the inclusion of an Omega 6:3 PUFA Blend thereby increasing the amount of long-chain omega-3 PUFAs that are delivered per serving.

As used herein, nutraceutical means a product isolated or purified from foods that is generally sold in medicinal forms not usually associated with food. As an example, the Omega 6:3 PUFA Blend, if encapsulated in a pill, would be a nutraceutical.

BRIEF DESCRIPTION OF THE DRAWINGS

FIG. 1 is a table of the master batch in grams.
FIG. 2 is a table of the master batch plus additibes in parts per million (ppm).
FIG. 3 is a table of the finished consumer product.

DETAILED DESCRIPTION

It is an object of the present invention to maximize the bioavailability and serving size of omega-3 long chain polyunsaturated fatty acids ("PUFAs") by preparing an omega-3 PUFA delivery system that minimizes adverse enzymatic and oxidation reactions from manufacturing to consumption of the delivery system and during consumption of the delivery system.

The Omega-6:3 PUFA Blend comprises a blend of oils with an aggregate omega-6 to omega-3 ratio between about 0.01:1 and about 4:1, a short chain omega-3 (ALA) to long chain omega-3 (DHA and/or EPA) ratio between about 0.01:1 and about 5:1, and at least 50 mg of long chain omega-3 PUFAs per serving of the functional food being enhanced. The Omega-6:3 PUFA Blends can also be incorporated into foods, pharmaceuticals, nutraceuticals, and/or the like.

In some embodiments, the Omega-6:3 PUFA Blend is incorporated into a composition for production of a food product. Particular, non-limiting examples of food products include mayonnaise or mayonnaise-like foods, salad dressing or salad dressing-like foods (including Ranch-style and Caesar), French and French-style dressings, pasta sauce, alfredo sauce, peanut butter and peanut butter-like foods, nut butter, and the like.

Oils Used in Making Oil Blends

High Oleic Peanut Oil, hereinafter referred to as "Peanut-Hi9," includes linoleic acid at a concentration that is less than about 3.5%, or less than about 3.2%, or less than about 2.95% on a weight basis, depending for which embodiment the Peanut-Hi9 is employed. The oleic acid component generally occupies greater than about 75% or greater than about 79% on a weight basis of the Peanut-Hi9. In other embodiments, oleic acid occupies about 75% or about 79% of the Peanut-Hi9.

High Oleic *Moringa Oleifera* seed oil, hereinafter referred to as "MO-Hi," has linoleic composition greater than about 3.0%, greater than about 2.0%, or greater than about 1.0% on a weight basis. In other embodiments, the oleic occupies about 70% or about 74% of the MO-Hi.

High linolenic Flax Oil, hereinafter referred to as "Flax-Hi3," has a linolenic to linoleic ratio that is about 6:1 or greater, or about 6.2:1 or greater, or about 6.4:1 or greater. Referring only to the linolenic content, the Flax-Hi3 is at least about 65% linolenic, or at least about 68% linolenic, or at least about 72% linolenic on a weight basis.

High oleic oils, hereinafter referred to as "Hi-9," from various producers are known in the art and may be utilized in the present invention. One particular high oleic oil, Plenish high oleic oil, is a product of Pioneer Hi-Bred International, Inc., a division of DuPont. The Plenish high oleic oil is a soybean oil that has at least about 75% oleic (18:1) on a weight basis, less than about 10% linoleic (18:2) on a weight basis, and less than about 3% linolenic (18:3) on a weight basis. In other embodiments, the oleic occupies about 75%, the linoleic occupies about 10%, and the linolenic occupies about 3% of the Hi-9 on a weight basis.

Omega-3 enriched oils (e.g., fish oil, concentrated fish oil, microalgae oil such as that available from Martek Biosciences Corporation, a division of DSM Nutritional Products AG, etc.) having a long chain omega-3 PUFA (DHA or EPA) content of at least about 20% on a weight basis may be utilized in the present invention. In some embodiments, omega-3 enriched oils having a long chain PUFA content approaching about 100% on a weight basis may be utilized. In other embodiments, omega-3 enriched oils or oil blends having a long chain omega-3 PUFA content of about 25%, of about 30%, of about 40%, of about 50%, of about 60%, of about 70%, of about 80%, or of about 90% are employed in the products and methods of the present invention.

The products and methods of the present invention do not incorporate any or minimally incorporate arachidonic acid, a long-chain omega-6 polyunsaturated fat (20:4 (ω-6)). An oil employed in the context of the present invention may contain trace amounts of arachidonic acid; but, in one embodiment, no end product or oil component of an end product manufactured in accordance with the present invention will include arachidonic acid at a level greater than about 20% on a weight basis relative to the total weight of omega-6 fatty acid. In another embodiment, the arachidonic acid present in an end product or oil component of an end product of the present invention will not exceed in weight about 10% of the total omega-6 fatty acid present. In yet another embodiment, the arachidonic acid present in an end product or oil component of an end product of the present invention will not exceed in weight about 5% of the total omega-6 fatty acid present.

Specific Omega-6:3 PUFA Blends

In a first embodiment, the Omega-6:3 PUFA Blend is a blend of at least two oils comprised of a first oil derived from flax seed and a second oil derived from a high oleic producing soy bean. The oil derived from flax seed is Flax-Hi3, where the Flax-Hi3 is less than about 8%, and in some embodiments less than about 7.5%, and in yet another embodiment, less than about 7.4% by weight basis of the Omega-6:3 PUFA Blend of the first embodiment. The second oil, Hi-9, occupies at least about 91% by weight basis of the first embodiment of the Omega-6:3 PUFA Blend. Accordingly, the Omega-6:3 PUFA Blend of the first embodiment has an oleic weight composition of at least about 60%, or at least about 63%, or at least about 64.5%. In another embodiment, the oil blend that combines a flax seed oil and a high oleic oil has an oleic weight composition that is about 60%, or about 63%, or about 64.5%.

In a second embodiment, the Omega-6:3 PUFA Blend is a blend of at least two oils comprised of a first oil derived from flax seed and a second oil derived from peanuts. The flax seed oil is the aforementioned Flax-Hi3, where the Flax-Hi3 has an approximately equal balance of omega-6 and omega-3 oils (i.e., a ratio of 1:1), or has a ratio of omega-6 to omega-3 oils where the omega-3 portion is greater than the omega-6 portion. The oil blend composition of the second embodiment has less than about 6% Flax-Hi3, or less than about 5% Flax-Hi3, or less than about 4% Flax-Hi3 by weight, combined with the Peanut-Hi9 that occupies at least about 95% of the oil blend by weight, such that the second embodiment oil blend has an oleic weight composition that is at least about 65%, or at least about 70%, or at least about 74%.

In a third embodiment, the Omega-6:3 PUFA Blend is a balanced Omega-6:Omega-3 oil that has a ratio of 1:1 or lower. This Omega 6:3 PUFA Blend comprises a first oil derived from flax seed, namely the aforementioned Flax-Hi3, and a second oil derived from the seed of a tree or bush known as *Moringa Oleifera*, namely the aforementioned MO-Hi. The Flax-Hi3 component occupies on a weight basis less than about 2% in one implementation, less than about 1.5% in a second implementation, or less than about 1% in a third implementation of this Omega 6:3 PUFA Blend. The second oil of MO-Hi occupies on a weight basis at least about 98% such that the blended third embodiment oil has an oleic weight basis of at least about 65% in one implementation, or at least about 70% in a second implementation, or at least about 72% in a third implementation.

One embodiment of the Omega-6:3 PUFA Blend is a concentrate comprised of multiple oils resulting in an omega-6 to omega-3 ratio from about 0.01:1 to about 4:1. In another embodiment, the ratio is between about 0.01:1 to about 1:1; in a third embodiment, the ratio is between about 0.5:1 to about 1:1; in a fourth embodiment, the ratio is between about 1:1 to about 4:1; in a fifth embodiment, the ratio is between about 1:1 to about 3:1; in a sixth embodiment, the ratio is between about 2:1 to about 3:1; in a seventh embodiment, the ratio is between about 2:1 to about 4:1; in an eighth embodiment, the ratio is between about 3:1 to about 4:1. Generally speaking, in view of the generally abundant sources of omega-6 PUFAs, the present invention emphasizes embodiments that have heightened omega-3 concentrations relative to the omega-6 concentration in a given Omega-6:3 PUFA Blend or prepared food.

In the various Omega 6:3 PUFA Blends set forth herein, the preferred second oil has an omega-9 to omega-6 ratio from about 5:1 to about 20:1, or from about 5:1 to about 15:1, or from about 5:1 to about 10:1, or from about 10:1 to about 20:1, or from about 15:1 to about 20:1. The second oil is blended with an omega-3 enriched oil (e.g., fish oil, concentrate fish oil, microalgae oil, etc.) having, on a weight basis, a long chain omega-3 PUFA content of at least 20%, or at least 25%, or at least 30%, or at least 40%, or at least 50%, or at least 60%, or at least 70%, or at least 80%, or at least 90%, or about 99% on a weight basis. In one embodiment, the specifically preferred second oil has less than about 5% or less than about 4%, or is about 3% or 2%, by weight of linolenic acid, in order to minimize oxidation between the time of manufacturing and the time of consumption. Linolenic acid, which is a short chain omega-3 PUFA, does not have a competing interaction with long chain omega-3 PUFAs, but as noted will adversely impacts shelf life.

In another embodiment, the second oil also has an omega-6 to omega-3 ratio from about 0.01:1 to about 4:1, or from about 0.01:1 to about 1:1; or from about 0.5:1 to about 1:1; or from about 1:1 to about 4:1; or from about 1:1 to about 3:1; or from about 2:1 to about 3:1; or from about 2:1 to about 4:1; or from about 3:1 to about 4:1; or from about 0.01:1 to about 0.24:1. Additionally, the second oil has and more preferably between 0.01 to 0.24; and an omega 9 to omega 6 ratio of at least about 5:1, i.e., for example, from about 50:1 to about 5:1, or from about 20:1 to about 5:1, or from about 50:1 to about 20:1.

In another embodiment, the second oil has an omega-6 to omega-3 ratio between about 0.01:1 and about 2.8:1; in a third embodiment, the ratio is between about 0.01:1 and about 1:1; in a fourth embodiment, the ratio is between about 1:1 and about 2:1; in a fifth embodiment, the ratio is between about 2:1 and about 3:1; in a sixth embodiment, the ratio is between about 1:1 and about 3:1; in a seventh embodiment, the ratio is between about 0.01:1 and about 2:1; in an eighth embodiment, the ratio is between about 0.01:1 and about 0.5:1.

In yet another embodiment, the second oil has an omega-9 to omega-6 ratio between about 5:1 and about 9:1; in a third embodiment, the ratio is between about 9:1 and about 25:1; in a fourth embodiment, the ratio is between about 50:1 and about 25:1; in a fifth embodiment, the ratio is between about 9:1 and about 25:1; in a sixth embodiment, the ratio is between about 40:1 and about 30:1; in a seventh embodiment, the ratio is between about 50:1 and about 40:1; and in an eighth embodiment, the ratio is between about 1:1 and about 5:1.

Another embodiment of the Omega 6:3 PUFA Blend is a concentrate comprised of multiple oils having an aggregate omega-9 to omega-3 ratio from greater than 4:1 to about 1:1, with at least 20% of the oil concentrate on a weight basis being long chain omega-3 PUFAs (i.e., DHA or EPA). The Omega 6:3 PUFA Blend is often utilized in a range of food systems, where it is desirable to maximize the omega-9 content, particularly when it displaces omega-6. The preferred omega-9 to omega-3 long chain PUFAs ratio of the second oil is from less than about 500:1 to about 1:1. In another embodiment, the second oil has an omega-9 to omega-3 long chain PUFA ratio between about 1:1 and about 100:1; in a third embodiment, the ratio is between about 1:1 and about 50:1; in a fourth embodiment, the ratio is between about 100:1 and about 500:1; in a fifth embodiment, the ratio is between about 1:1 and about 200:1; in a sixth embodiment, the ratio is between about 200:1 and about 400:1; in a seventh embodiment, the ratio is between about 1:1 and about 300:1; in an eighth embodiment, the ratio is between about 50:1 and about 300:1; and in a ninth embodiment, the ratio is between about 50:1 and about 200:1. In another embodiment, the second oil has a composition of at least about 70% oleic acid. Another embodiment of the second oil consistent with this embodiment contains at least about 70% oleic acid, less than about 4% linolenic acid, and less than about 4% linoleic acid.

The presence of omega-3 fatty acid in an oil blend tends to minimize the stability of the oil blend due to the propensity of the omega-3 fatty acids to turn rancid. Accordingly, a balanced omega-6 to omega-3 ratio with reasonable stability characteristics can result in an Omega 6:3 PUFA Blend that contains less than about 6% by weight of linolenic acid and where the omega-6 to omega-3 ratio is from about 0.5:1 to about 1:1. In another embodiment, the omega-6 to omega-3 ratio is between about 0.01:1 and about 0.5:1; in a third embodiment, the ratio is between about 0.01:1 and about 1:1; in a fourth embodiment, the ratio is between about 0.5:1 and about 2:1; in a fifth embodiment, the ratio is between about 0.01:1 and about 2:1; in a sixth embodiment, the ratio is between about 0.5:1 and about 0.75:1; and in a seventh embodiment, the ratio is between about 0.75:1 and about 1:1. In another embodiment, the Omega 6:3 PUFA Blend that contains less than about 4% linolenic or less than about 2% linolenic by weight basis.

In another embodiment of the present invention, a balanced omega-6 to omega-3 ratio is achieved by maximizing the weight percentage of oleic acid, wherein, for example, the oleic weight percentage basis is greater than about 60%. In other embodiments, the oleic weight basis is greater than about 65% or greater than about 70%.

In yet another embodiment, the second oil has an omega-9 to omega-6 ratio greater than about 9:1, or greater than about 25:1. In this embodiment, the second oil has an omega-9 to omega-6 ratio between about 5:1 and about 9:1; or between about 9:1 and about 25:1; or between about 50:1 and about 25:1; or between about 9:1 and about 25:1; or between about 40:1 and about 30:1; or between about 50:1 and about 40:1; or between about 1:1 and about 5:1. The first oil has a linolenic weight percentage greater than about 70%.

Specific exemplar formulations of the Omega-6:3 PUFA Blend include at least a first oil and a second oil resulting in a blended oil having an omega-6 to omega-3 ratio from about 0.01:1 to about 4:1, and having a blended composition of: 1) at least about 60% oleic acid, at least about 0.5% linolenic acid, and at most about 8.0% linoleic acid; or 2) at least about 65% oleic acid, at most about 8.0% linolenic acid, and at most about 4.0% linoleic acid; or 3) at least about 65% oleic acid, at most about 4.0% linoleic acid, and at most about 2.0% linoleic acid. In another exemplar embodiment, the ratio of omega 6 to omega 3 is between about 0.01:1 and about 1:1; in a third embodiment, the ratio is between about 0.5:1 and about 1:1; in a fourth embodiment, the ratio is between about 1:1 and about 4:1; in a fifth embodiment, the ratio is between about 1:1 and about 3:1; in a sixth embodiment, the ratio is between about 2:1 and about 3:1; in a seventh embodiment, the ratio is between about 2:1 and about 4:1; in an eighth embodiment, the ratio is between about 3:1 and about 4:1.

In yet another embodiment, the Omega-6:3 PUFA Blend contains a third oil having an omega-3 long chain PUFA weight basis of at least about 20 percent to about 100 percent; alternative compositions of the third oil include omega-3 long-chain PUFA weight basis of at least about 25%, or at least about 30%, or at least about 40%, or at least about 50%, or at least about 60%, or at least about 70%, or at least about 80%, or at least about 90%, or about 99%. The preferred oil maximizes the weight percent of omega-3 long chain PUFAs, more preferably high in DHA and EPA and low in omega-6. The Omega-6:3 PUFA Blend is subsequently added to a wide range of consumer products including food, beverage, nutritional supplement, or pharmaceutical products having a long chain omega-3 (i.e., DHA and EPA) dosage of greater than 50 mg per standard serving. The preferred Omega-6:3 PUFA Blend formulations, notably for food products that are rich in oil (e.g., mayonnaise, salad dressings, peanut butter, etc.), utilize oils having an aggregate omega-6 to linolenic ratio of less than about 3:1, an aggregate omega-9 to linolenic ratio of less than about 10:1, and an aggregate omega-6 to long chain omega-3 PUFAs ratio of less than about 0.5:1.

Antioxidants

Antioxidants are often added to fat-containing foods to delay the onset or slow the development of rancidity due to oxidation. Natural antioxidants include polyphenols (for instance flavonoids), ascorbic acid (vitamin C) and mixed tocopherols (vitamin E). Synthetic antioxidants include butylated hydroxyanisole (BHA), butylated hydroxytoluene (BHT), tert-butylhydroquinone (TBHQ), propyl gallate, and ethoxyquin. The natural antioxidants tend to be short-lived, so synthetic antioxidants are used when a longer shelf-life is preferred. The effectiveness of water-soluble antioxidants is limited in preventing direct oxidation within fats, but is valuable in intercepting free radicals that travel through the watery parts of foods.

Another embodiment of the Omega-6:3 PUFA Blend incorporates at least 2% of pineapple juice on a weight basis to the omega-3 long chain PUFA weight. A preferred formulation further comprises a sinapyl compound including the sinapyl compound as isolated from pineapple juice. In many embodiments of the present invention, the oil blend formulation does not include pineapple juice. One alternative is to include a sinapyl compound as isolated from pineapple juice into the Omega-6:3 PUFA Blend. Alternatively, the Omega-6:3 PUFA Blend can contain a sulfur containing antioxidant particularly when iron is present in the food, beverage, nutritional supplement, or pharmaceutical products; one such sulfur-containing antioxidant usefully employed herein is isolated from broccoli. Yet another alternative antioxidant usefully employed with the present invention contains at least one of sulforaphane and a sulforaphane precursor glucosinolate, such as sulforaphane glucosinolate. Another embodiment of antioxidant used in the context of the present invention is ferulic acid, particularly from coffee fruit.

It is well known in the art, that the vast majority of antioxidants when utilized at high levels become pro-oxidant. The invention disclosed establishes a unique blend of antioxidant and low omega-6 and omega-3 short chain oil that avoids the pro-oxidant condition as compared to individual usage levels, particularly of Vitamin E (i.e., mixed tocopherols). One such inventive embodiment is the inclusion of inositol on a weight basis of a range of about 25 ppm to about 100 ppm with Vitamin E included in a range of about 50 ppm to about 200 ppm; in another embodiment, the inositol is included in the oil blend at about 50 ppm and the Vitamin E is included in the oil blend at about 100 ppm.

In one embodiment, the blend of antioxidant is a curcumin C3 complex on a weight basis of from about 5 ppm to about 20 ppm, inositol on a weight basis of from about 25 ppm to about 100 ppm, and Vitamin E of from about 50 ppm to about 200 ppm. For example, in an example of this embodiment, the blend of antioxidant comprises at least about 10 ppm, inositol on a weight basis of at least about 50 ppm, and Vitamin E of at least about 100 ppm.

Naturally occurring antioxidants can also be readily incorporated into the present invention. In addition to Vitamin E compositions, which typically are a blend of tocopherols, but predominantly alpha-tocopherol, one can readily employ Rosemary, for example.

One can also employ synthetic antioxidants, such as, for example, butylated hydroxyanisole ("BHA"), butylated hydroxytoluene ("BHT"), and tert-butylhydroquinone ("TBHQ").

Another embodiment includes an antioxidant blend of a manganese oxide emitting a blue color at ambient temperatures on a weight basis of at least about 10 ppm, inositol on a weight basis of at least about 50 ppm and Vitamin E of at least about 100 ppm.

Another approach to stabilizing the oil blends used in the context of the present invention includes use of oxygen scavengers to reduce the amount of oxygen present for oxidation of the oil. For example, one could include ascorbic acid for this purpose.

One can also extend the time of stabilized product by microencapsulation of the omega-3 oils using starch or protein; or, alternatively, using medium chain triglycerides as the encapsulating agent, using methods well-known in the art.

It is also possible, and absolutely outside the scope of the present invention, to extend the shelf-life of product (i.e., extend stabilization characteristic) by reducing the levels of included omega-3 oil present to miniscule levels or to add flavors or aromas to mask rancidity.

For example, a product having about 32 mg per serving of omega-3 oil or less can have a very long shelf-life, literally disposed to a shelf-life of years.

In contrast, any product manufactured in accordance with this disclosure will include per standard serving portion at least about 50 mg of omega-3 long chain oil, or at least about 60 mg of omega-3 long chain oil, or at least about 70 mg of omega-3 long chain oil, or at least about 80 mg of omega-3 long chain oil, or at least about 90 mg of omega-3 long chain oil, or at least about 100 mg of omega-3 long chain oil, or at least about 110 mg of omega-3 long chain oil, or at least about 120 mg of omega-3 long chain oil, or at least about 130 mg of omega-3 long chain oil. Such a product having concentration of long chain omega-3 oil to deliver in a standard serving portion of the end product functional food at least about 50 mg of omega-3 long chain oil will not be stable enough to be transported from the point of manufacture to the retail sales outlets, let alone have a shelf-life of at least about eight months. Even more so, a product manufactured in accordance with the present invention having 75 mg, or 85 mg, or 95 mg, on up to at least 125 mg of omega-3 long chain oil per standard serving size will have a shelf-life of from about eight months at minimum to about 10 months, or 12 months, or 14 months, or 16 months, or 18 months, or more. Variations in shelf-life maximum exist on a per product basis, but not one product manufactured in accordance with the present disclosure has a shelf-life of less than about eight months.

Emulsions

The Omega-6:3 PUFA Blend is commonly used in the context of an emulsion, wherein the oil blend is prepared oil into an emulsion, such as a microemulsion or a nanoemulsion; accordingly, the antioxidant is subsequently added to the water phase with the already prepared Omega-6:3 PUFA Blend micro- or nano-emulsion. One method usefully employed for preparing the emulsion is the addition of medium chain triglyceride at a weight ratio to omega-3 long chain PUFA of at least about 0.01:1 to about 4:1, and an emulsifier at a ratio to omega-3 long-chain PUFA of at least 0.01:1 to about 4:1. In another embodiment, the ratio is between about 0.01:1 and about 1:1; in a third embodiment, the ratio is between about 0.5:1 and about 1:1; in a fourth embodiment, the ratio is between about 1:1 and about 4:1; in a fifth embodiment, the ratio is between about 1:1 and about 3:1; in a sixth embodiment, the ratio is between about 2:1 and about 3:1; in a seventh embodiment, the ratio is between about 2:1 and about 4:1; in an eighth embodiment, the ratio is between about 3:1 and about 4:1. The prepared micro- or nano-emulsion is then added to a food, thus forming a functional food, or a beverage, or a nutraceutical, or a pharmaceutical at a level of at least about 50 mg of omega-3 long chain PUFAs per serving. Alternative embodiments of such products will include the micro- or nano-emulsion added such that the resultant functional food or nutraceutical or pharmaceutical includes per serving or pill at least about 60 mg, or at least about 70 mg, or at least about 80 mg, or at least about 90 mg, or at least about 100 mg, or at least about 110 mg, or at least about 120 mg, or at least about 130 mg.

The addition of inositol at a level of at least about 50 ppm to about 400 ppm into the oil phase prior to creating the micro- or nano-emulsion provides another tool for limiting a pro-oxidant condition when utilizing Vitamin E at levels greater than about 100 ppm, and particularly at levels greater than about 300 ppm. In particular, when including tocotrienols in addition or instead of the mixed tocopherols that the formulation labeled Vitamin E commonly is, it is highly desirable to include the inositol at the recited proportions with respect to Vitamin E.

Triglyceride Recrystallized Phytosterols

It is known in the art that a high level of phytosterols provides oxidative stability benefits to omega-3, but excessive levels detract from the efficacy of omega-3. In one embodiment, phytosterols are employed at relatively low levels, such as, for example, where the phytosterols component constitutes no more than about 24% by weight. It is also known that phytosterols converted from non-esterified phytosterols to triglyceride-recrystallized phytosterols provide superior performance; the present invention includes, in one embodiment, the use of recrystallized phytosterols that are converted from non-esterified phytosterols to triglyceride-recrystallized phytosterols using medium chain triglycerides. The triglyceride-recrystallized phytosterols is infused into the Omega-6:3 PUFA Blend by the following:

a. Adding the triglyceride-recrystallized phytosterols to at least 10% by weight of carbon dioxide,
b. Increasing the pressure of the combined triglyceride-recrystallized phytosterols and carbon dioxide to a pressure at least 3 psi greater than the supercritical pressure of carbon dioxide and a temperature of at least 2° F. greater than the supercritical temperature of carbon dioxide,
c. Adding the combined triglyceride-recrystallized phytosterols and carbon dioxide supercritical mixture to the omega-3 long-chain PUFA under rapid expansion conditions to concurrently recrystallize the phytosterols to crystal size of less than about 1000 nm to about 20 nm and decreasing the temperature of the triglyceride-recrystallized phytosterols to less than 40° C. within 60 seconds.

Preparation of Specific Food Products

In some embodiments, an Omega-6:3 PUFA Blend of the present application is utilized with base products for the preparation of various food products, such as, for example and without limitation, mayonnaise, salad dressings, pasta sauces, peanut butter, and the like. Food products such as these may have specific requirements to be classified as the type of product, but there is wide latitude for specific alterations to achieve desirable sensory attributes (e.g., taste, smell, feel, etc.). Such sensory attributes can be achieved through the later addition of spices, alteration of oil percentage, and the like, to prepare a finished food product. As herein contemplated, the Omega-6:3 PUFA Blend is utilized in the creation of the base compositions of various food products.

Also contemplated are variations on standard recipes or requirements, such as mayonnaise-like food products, salad dressing-like food products, French dressing-like food products, peanut butter-like food products, etc., where variation from established standards are not generally substantive as to the nature of the food product at issue.

In some embodiments, the present invention is designed to deliver at least about 50 mg of long chain omega-3 PUFAs (i.e., DHA and EPA) per standard serving (e.g., 1 tbsp mayonnaise, 2 tbsp peanut butter, 2 tbsp salad dressing, etc.). Specific formulations of Omega-6:3 PUFA Blends may be adapted to achieve the minimum dose of long chain omega-3 PUFAs per serving in different products (e.g., blend for mayonnaise must be different from blend for salad dressing). In particular, the present invention contemplates use of the Omega-6:3 PUFA Blends in a manner consistent with this disclosure for the manufacture of functional food products that deliver about 50 mg of DHA or EPA per serving, or about 60 mg of DHA or EPA per serving, or about 70 mg of DHA or EPA per serving, or about 80 mg of DHA or EPA per serving, or about 90 mg of DHA or EPA per serving, or about 100 mg of DHA or EPA per serving, or about 110 mg of DHA or EPA per serving, or about 120 mg of DHA or EPA per serving, or about 130 mg of DHA or EPA per serving. In yet another alternative embodiment, each of the aforementioned levels of DHA or EPA delivered per serving are considered minimums.

In some embodiments, the food base product being made is produced by combining various groupings of ingredients. Exemplary groupings include oil phase ingredients, dry or powder phase ingredients, water phase ingredients, acid phase ingredients, and/or the like.

Oil Phase

Oil phase ingredients include, obviously, any oil(s) incorporated into the food base product. This would be any high oleic oil, any fish oil, any vegetable oil, any Omega-6:3 PUFA Blend, any hydrogenated or partially hydrogenated vegetable oil, butter, and the like. Also present in the oil phase would be any alpha-tocopherols, tocopherols, tocotrienols, medium chain triglycerides, and the like. Other ingredients usefully employed to potentiate stabilization of the oil phase ingredients can also be added, such as, for example, the inositol.

Dry or Powder Phase

Dry or powder phase ingredients include: onion powder, garlic powder, citric acid, salt, sugar, dried egg, egg yolk powder, spices, sodium benzoate, potassium sorbate, natural flavors, gums, starches, high oleic roasted peanuts, sodium hexametaphosphate, whey protein, some acid phase ingredients, parmesan cheese, cheese blend, dried onions, dried garlic, polyglycol alginate, yeast extract, diced tomatoes, tomato paste, anchovy paste, caramel color, and the like.

Acid Phase

Acid phase ingredients include: lemon juice, vinegar, lactic acid, citric acid, phosphoric acid, and the like.

Water Phase

Water phase ingredients include: water, sugar, salt, xanthan gum, EDTA, liquid egg, liquid egg yolk, sodium benzoate, potassium sorbate, natural flavors, gums, starches, buttermilk, acid phase ingredients, tomato paste, FD&C red 40, heavy cream, butter, sodium hexametaphosphate, whey protein, parmesan cheese, cheese blend, polyglycol alginate, diced tomatoes, anchovy paste, caramel color, and the like.

Example Food Products

Mayonnaise Base Product

The standard for identity of mayonnaise is governed by 21 CFR 169.140, as issued by the FDA. Per 21 CFR 169.140, mayonnaise must contain at least 65% by weight of vegetable oil, an acidifying ingredient (selected from vinegar of at least 2.5% acidity or lemon/lime juice of at least 2.5% acidity), and egg yolk-containing ingredients. Mayonnaise may also contain any of the following: salt; nutritive carbohydrate sweeteners; any spice (except saffron or turmeric) or natural flavoring, provided it does not impart to the mayonnaise a color simulating the color imparted by egg yolk; monosodium glutamate; sequestrant(s), including but not limited to calcium disodium EDTA (calcium disodium ethylenediamine-tetraacetate) and/or disodium EDTA (disodium ethylenediaminetetraacetate), may be used to preserve color and/or flavor; citric and/or malic acid in an amount not greater than 25 percent of the weight of the acids of the vinegar or diluted vinegar, calculated as acetic acid; and crystallization inhibitors, including but not limited to oxystearin, lecithin, or polyglycerol esters of fatty acids.

Mayonnaise or mayonnaise-like food products with at least 50 mg of long chain omega-3 (EPA/DHA) per serving (13 g for mayonnaise or mayonnaise-like products) shall contain the following: Omega-6:3 PUFA Blend as at least 50.773% by weight of the mayonnaise or mayonnaise-like finished food product. A mayonnaise or mayonnaise-like food product with at least 68.870% by weight Omega-6:3 PUFA Blend delivers 107 mg DHA and EPA per 13 g serving, has a short chain omega-3 to long chain omega-3 ratio of about 0.65:1, and has an overall omega-6 to omega-3 ratio of about 3.62:1.

The mayonnaise base product recipe may be completed by the addition of additional ingredients (new or previously included) in proportions necessary to maintain the omega-3 and omega-6 ratios and levels.

The mayonnaise base product is processed into a finished food product by adding to a mix tank the water phase ingredients. Liquid whole egg is added to the mixing tank. Omega-6:3 PUFA Blend is then added to the mixing tank. All ingredients are mixed well, and then run through a colloid mill. The batch is then pumped to storage tanks prior to packaging the finished food product.

Caesar Dressing Base Product

The standard of identity for salad dressings is governed by 21 CFR 169.150, as issued by the FDA. Per 21 CFR 169.150, salad dressing is the emulsified semisolid food prepared from at least 30% by weight vegetable oil(s), an acidifying ingredient (vinegar or lemon/lime juice), egg yolk-containing ingredients (Liquid egg yolks, frozen egg yolks, dried egg yolks, liquid whole eggs, frozen whole eggs, dried whole eggs, or any one of more of the foregoing ingredients listed in this paragraph with liquid egg white or frozen egg white) equivalent to at least 4% by weight of liquid egg yolks, and a starchy paste (which may be prepared from one or more of may be prepared from a food starch, food starch-modified, tapioca flour, wheat flour, rye flour, or any two or more of these, and optionally water). Salad dressing may also contain one or more of the following ingredients: salt; nutritive carbohydrate sweeteners; any spice (except saffron or turmeric) or natural flavoring, provided it does not impart to the salad dressing a color simulating the color imparted by egg yolk; monosodium glutamate; stabilizers and thickeners (Dioctyl sodium sulfosuccinate may be added); citric and/or malic acid may be used in an amount not greater than 25 percent of the weight of the acids of the vinegar or diluted vinegar calculated as acetic acid; sequestrant(s), including but not limited to calcium disodium EDTA (calcium disodium ethylenediamine-tetraacetate) and/or disodium EDTA (disodium ethylenediamine-tetraactetate), may be used to preserve color and/or flavor; crystallization inhibitors, including but not limited to oxystearin, lecithin, or polyglycerol esters of fatty acids.

Salad dressing or salad dressing-like food products can be prepared with the Omega-6:3 PUFA Blend. One example is a Caesar salad dressing or salad dressing-like food product. A Caesar salad dressing or salad dressing-like food product with at least 50 mg DHA/EPA per serving (32 g for Caesar salad dressing or salad dressing-like food products) shall contain the following: Omega-6:3 PUFA Blend as at least 33.755% by weight of the Caesar salad dressing or salad dressing-like food products. A Caesar salad dressing or salad dressing-like food products with at least 47.280% by weight Omega-6:3 PUFA Blend delivers 126 mg DHA and EPA per 32 g serving, has a short chain omega-3 to long chain omega-3 ratio of about 2.05:1, and has an overall omega-6 to omega-3 ratio of about 2.97:1.

The Caesar dressing base product recipe may be completed by the addition of additional ingredients (new or previously included) in proportions necessary to maintain the omega-3 and omega-6 ratios and levels.

The Caesar salad dressing base food product is processed into a finished food product by adding to a mixing tank all water phase ingredients. The agitator in the mixing tank is turned on, and the starchy paste is added and distributed. The rest of the dry ingredients are added to the mixing tank, and the batch is mixed until the dry ingredients have dissolved. The Omega-6:3 PUFA Blend is then added to the mixing tank, and the batch is run through a colloid mill. The batch is then pumped into a particle tank, where spices are added, and then the finished food product is packaged.

Pasta Sauce Base Product

No standard of identity has been issued by the FDA for pasta sauce. A typical formulation would contain some combination of the following: water, tomato paste (24 NTSS), diced tomatoes, sugar, salt, dried garlic, spices, dried onion, citric acid (anhydrous), and natural flavors.

Pasta sauce can be prepared with the Omega-6:3 PUFA Blend. A pasta sauce with at least 50 mg DHA/EPA per serving (126 g for pasta sauce) shall contain the following: Omega-6:3 PUFA Blend as at least 0.336% by weight of the pasta sauce food products. A pasta sauce food product with at least 2.330% by weight Omega-6:3 PUFA Blend delivers 103 mg DHA and EPA per 126 g serving, has a short chain omega-3 to long chain omega-3 ratio of about 0.33:1, and an overall omega-6 to omega-3 ratio of about 1.56:1.

The pasta sauce base product recipe may be completed by the addition of additional ingredients (new or previously included) in proportions necessary to maintain the omega-3 and omega-6 ratios and levels.

The pasta sauce base food product is processed into a finished food product by adding water phase ingredients to a batch tank. The contents of the batch tank are mixed until uniform. Once uniform, the Omega-6:3 PUFA Blend is added to the batch, which is then run through the tube in a tube heat processor and into the filler hold tank prior to packaging the finished food product.

Alfredo Sauce Base Product

No standard of identity has been issued by the FDA for alfredo sauce. A typical formulation would contain some combination of the following: Milk or Cream, Cheese (Parmesan, Romano or other type of cheese to impart flavor), Salt, Sugar, Phosphate Source to help in dissolving cheese to make a smoother sauce, Sodium Phosphate or Sodium Hexametaphosphate, Butter (salted or unsalted), Natural Flavors, Yeast Extracts, Spices, Dried Onions, Dried Garlic, Gums, Starches, Whole Liquid Egg and Dried Egg products, Whey Proteins, Dried Milk Powder, Shortening Powder.

Alfredo Sauce with at least 50 mg of long chain omega-3 (EPA/DHA) per serving (126 g for alfredo sauce) shall contain the following: Omega-6:3 PUFA Blend as at least 0.35% by weight of the alfredo sauce finished food product. An alfredo sauce with at least 1.05% by weight Omega-6:3 PUFA Blend delivers 168 mg DHA and EPA per 126 g serving, has a short chain omega-3 to long chain omega-3 ratio of about 0.70:1, and has an overall omega-6 to omega-3 ratio of about 1.93:1.

The alfredo sauce base product recipe may be completed by the addition of additional ingredients (new or previously included) in proportions necessary to maintain the omega-3 and omega-6 ratios and levels.

The alfredo sauce base food product is processed into a finished food product by adding to a mixing tank all water phase ingredients. The agitator in the mixing tank is turned on, and the starchy paste is added and distributed. The rest of the dry ingredients are added to the mixing tank, and the batch is mixed until the dry ingredients have dissolved. The Omega-6:3 PUFA Blend is then added to the mixing tank, and the batch is run through a colloid mill. The batch is then pumped into a particle tank, where spices are added, and then the finished food product is packaged. The recipe is made by adding to a high shear mixer tank, in order, water and phosphates. The water and phosphates are mixed for 15 to 30 minutes until all phosphates have been dissolved. Cheese is then added to the high shear mixer tank, which is run until all cheese has been fully dissolved (antifoam is used if necessary). All ingredients except spices and natural flavors are then added to the high shear mixer tank, which is run until all ingredients are uniform. The batch is then transferred to a mix tank, where spices and natural flavor are added. The batch is then run through the tube in a tube heat exchanger and heated prior to packaging the finished food product.

Red French-style Dressing Base Product

The standard for identity of French dressing is governed by 21 CFR 169.115, as issued by the FDA. Per 21 CFR 169.115, French dressing is the separable liquid food or the emulsified viscous fluid food prepared from at least 35% by weight vegetable oil(s) and an acidifying ingredient (vinegar or lemon/lime juice). French dressing may also contain one or more of the following ingredients: salt; nutritive carbohydrate sweeteners; spices and/or natural flavorings; monosodium glutamate; tomato paste, tomato puree, catsup, sherry wine; eggs and ingredients derived from eggs; color additives that will impart the color traditionally expected; stabilizers and thickeners to which calcium carbonate or sodium hexametaphosphate may be added, and Dioctyl sodium sulfosuccinate may be added; citric and/or malic acid, in an amount not greater than 25 percent of the weight of the acids of the vinegar or diluted vinegar calculated as acetic acid; sequestrant(s), including but not limited to calcium disodium EDTA (calcium disodium ethylenediamine-tetraacetate) and/or disodium EDTA (disodium ethylenediamine-tetraacetate), may be used to preserve color and/or flavor; crystallization inhibitors, including but not limited to oxystearin, lecithin, or polyglycerol esters of fatty acids.

French or French-style dressing with at least 50 mg of long chain omega-3 (EPA/DHA) per serving (32 g for French or French-style dressing products) shall contain the following: Omega-6:3 PUFA Blend as at least 10.398% by weight of the French or French-style dressing product. A French or French-style dressing product with at least 18.3% by weight Omega-6:3 PUFA Blend delivers 101 mg DHA and EPA per 32 g serving, has a short chain omega-3 to long chain omega-3 ratio of about 1.46:1, and has an overall omega-6 to omega-3 ratio of about 1.9:1.

The red French style dressing base product recipe may be completed by the addition of additional ingredients (new or previously included) in proportions necessary to maintain the omega-3 and omega-6 ratios and levels.

The French-style dressing base food product is processed into a finished food product by adding to a mixing tank all water phase ingredients. The agitator in the mixing tank is turned on, and the starchy paste is added and distributed. The rest of the dry ingredients are added to the mixing tank, and the batch is mixed until the dry ingredients have dissolved. The Omega-6:3 PUFA Blend is then added to the mixing tank, and the batch is run through a colloid mill. The batch is then pumped into a particle tank, where spices are added, and then the finished food product is packaged.

Ranch-style Salad Dressing Base Product

The standard of identity for salad dressings is governed by 21 CFR 169.150, as issued by the FDA. Per 21 CFR 169.150, salad dressing is the emulsified semisolid food prepared from at least 30% by weight vegetable oil(s), an acidifying ingredient (vinegar or lemon/lime juice), egg yolk-containing ingredients (Liquid egg yolks, frozen egg yolks, dried egg yolks, liquid whole eggs, frozen whole eggs, dried whole eggs, or any one of more of the foregoing ingredients listed in this paragraph with liquid egg white or frozen egg white) equivalent to at least 4% by weight of liquid egg yolks, and a starchy paste (which may be prepared from one or more of may be prepared from a food starch, food starch-modified, tapioca flour, wheat flour, rye flour, or any two or more of these, and optionally water). Salad dressing may also contain one or more of the following ingredients: salt; nutritive carbohydrate sweeteners; any spice (except saffron or turmeric) or natural flavoring, provided it does not impart to the salad dressing a color simulating the color imparted by egg yolk; monosodium glutamate; stabilizers and thickeners (Dioctyl sodium sulfosuccinate may be added); citric and/or malic acid may be used in an amount not greater than 25 percent of the weight of the acids of the vinegar or diluted vinegar calculated as acetic acid; sequestrant(s), including but not limited to calcium disodium EDTA (calcium disodium ethylenediamine-tetraacetate) and/or disodium EDTA (disodium ethylenediamine-tetraactetate), may be used to preserve color and/or flavor; crystallization inhibitors, including but not limited to oxystearin, lecithin, or polyglycerol esters of fatty acids.

Salad dressing or salad dressing-like food products can be prepared with the Omega-6:3 PUFA Blend. One example is a Ranch-style salad dressing or salad dressing-like food product. A Ranch-style salad dressing or salad dressing-like food product with at least 50 mg DHA/EPA per serving (30 g for Ranch-style salad dressing or salad dressing-like food products) shall contain the following: Omega-6:3 PUFA Blend as at least 47.121% by weight of the Ranch-style salad dressing or salad dressing-like food products. A Ranch-style salad dressing or salad dressing-like food products with at least 59.52% by weight Omega-6:3 PUFA Blend delivers 112 mg DHA and EPA per 30 g serving, has a short chain omega-3 to long chain omega-3 ratio of about 4.09:1, and has an overall omega-6 to omega-3 ratio of about 3.19:1.

The Ranch style dressing base product recipe may be completed by the addition of additional ingredients (new or previously included) in proportions necessary to maintain the omega-3 and omega-6 ratios and levels.

The Ranch-style salad dressing base food product is processed into a finished food product by adding to a mixing tank all water phase ingredients. The agitator in the mixing tank is turned on, and the starchy paste is added and distributed. The rest of the dry ingredients are added to the mixing tank, and the batch is mixed until the dry ingredients have dissolved. The Omega-6:3 PUFA Blend is then added to the mixing tank, and the batch is run through a colloid mill. The batch is then pumped into a particle tank, where spices are added, and then the finished food product is packaged.

Peanut Butter Base Product

The standard of identity for peanut butter is governed by 21 CFR 164.150, as issued by the FDA. Per 21 CFR 164.150, peanut butter is the food prepared by grinding shelled and roasted peanut ingredients (blanched peanuts, in which the germ may or may not be included; or unblanched peanuts, including the skins and germ), to which may be added safe and suitable seasoning and stabilizing ingredients, but such seasoning and stabilizing ingredients do not in the aggregate exceed 10 percent of the weight of the finished food. To the ground peanuts, cut or chopped, shelled, and roasted peanuts may be added. During processing, the oil content of the peanut ingredient may be adjusted by the addition or subtraction of peanut oil. The fat content of the finished food shall not exceed 55 percent. Seasoning and stabilizing ingredients that perform a useful function are regarded as suitable, except that artificial flavorings, artificial sweeteners, chemical preservatives, and color additives are not suitable ingredients in peanut butter. Oil products used as optional stabilizing ingredients shall be hydrogenated vegetable oils. Hydrogenated vegetable oil is considered to include partially hydrogenated vegetable oil.

Peanut butter or peanut butter-like food products can be prepared with the Omega-6:3 PUFA Blend. A peanut butter or peanut butter-like food product with at least 50 mg DHA/EPA per serving (32 g for peanut butter or peanut butter-like food products) shall contain the following: Omega-6:3 PUFA Blend as at least 0.710% by weight of the peanut butter or peanut butter-like food products. A peanut butter or peanut butter-like food product with at least 1.250% by weight Omega-6:3 PUFA Blend (considering delivers 105 mg DHA and EPA per 32 g serving, has a short chain omega-3 to long chain omega-3 ratio of about 2.53:1, and an overall omega-6 to omega-3 ratio of about 2.9:1.

The peanut butter base product recipe may be completed by the addition of additional ingredients (new or previously included) in proportions necessary to maintain the omega-3 and omega-6 ratios and levels.

The base food product is processed into a finished food product by mixing all ingredients in a mixing tank until uniform, after which the blended peanut butter is run through a tubular cooler and then pumped into a storage tank, prior to packaging.

What is claimed is:

1. A composition for manufacture of a food product, consisting essentially of:
   a. A first oil comprising omega-6 fatty acids in a canned/jarred food product;
   b. A second oil comprising omega-3 fatty acids in the canned/jarred food product; and
   c. An antioxidant in the canned/jarred food product; wherein the ratio of omega-6 fatty acids by weight to omega-3 fatty acids by weight is from 0.01:1 to 0.65:1; the omega-3 fatty acids comprise a short-chain polyunsaturated fatty acid ("PUFA") and a long-chain PUFA, where the short chain has fewer than 20 carbon atoms in an aliphatic tail and the long chain PUFA has greater than 20 carbons in an aliphatic tail, where the ratio of long-chain PUFA by weight to short-chain PUFA by weight is from 1:5 to 1:0.01; and the canned/jarred food product contains at least 50 mg of long-chain PUFA per 13 g serving size of the canned/jarred food product.

2. The composition of claim 1, wherein the antioxidant is selected from the group consisting of:
   a. A sinapyl compound;
   b. A sulfur containing antioxidant;
   c. A ferulic acid containing antioxidant;
   d. Vitamin E;
   e. a tocotrienol; or
   f. curcumin.

3. The composition of claim 2, wherein the sulfur containing antioxidant is isolated from broccoli.

4. The composition of claim 1, further comprising at least one of vegetal chitosan and chitin-glucan at 0.1% to 4.0% by weight of the first oil, wherein the at least one of vegetal chitosan and chitin-glucan is mixed into the first oil prior to being incorporated into the composition.

5. The composition of claim 1, wherein the canned/jarred food product is mayonnaise, or a salad dressing, French dressing, or peanut butter, or nut butter, or pasta sauce.

6. The composition of claim 5, wherein the salad dressing is Ranch or Caesar.

7. A processed food base for producing a finished mayonnaise, comprising the composition of claim 1, an acidifying ingredient, and an egg yolk-containing ingredient; wherein a standard serving portion of the finished mayonnaise contains at least 50 mg of long-chain PUFAs; and the base product comprises at least 65% by weight vegetable oil.

8. A processed food base product for producing a finished salad dressing, comprising the composition of claim 1, an acidifying ingredient, an egg yolk-containing ingredient, and a starchy paste; wherein a standard serving portion of the finished salad dressing contains at least 50 mg of long-chain PUFAs; and the base product contains at least 30% by weight of vegetable oil and at least egg yolk solids equivalent to 4% by weight of liquid egg yolks.

9. A processed food base for producing a finished French dressing, comprising the composition of claim 1 and an acidifying ingredient, wherein a standard serving portion of the finished French dressing contains at least 50 mg of long-chain PUFAs and the base product contains at least 35% by weight of vegetable oil.

10. A processed food base for producing a finished peanut butter, comprising the composition of claim 1, ground shelled and roasted peanut ingredient, seasoning and stabilizing ingredients in aggregate of less than 10% of the weight of the finished food; wherein the oil content of the peanut ingredient may be adjusted by the addition or subtraction of peanut oil, such that the fat content of the finished food shall not exceed 55%, and the addition of peanut oil is included in the composition of claim 1, and a standard serving portion of the finished peanut butter contains at least 50 mg of long-chain PUFAs.

11. A composition for manufacture of a food product, consisting essentially of:
   a. A first oil comprising omega-6 fatty acids in a canned/jarred food product;
   b. A second oil comprising omega-3 fatty acids in the canned/jarred food product; and
   c. An antioxidant in the first oil and the second oil; wherein the ratio of omega-6 fatty acids by weight to omega-3 fatty acids by weight is from 0.67:1 to 5:1; the omega 3 fatty acids comprise a short-chain polyunsaturated fatty acid ("PUFA") and a long-chain PUFA, where the short chain has fewer than 20 carbon atoms in an aliphatic tail and the long chain PUFA has greater than 20 carbons in an aliphatic tail where the ratio of long-chain PUFA by weight to short-chain PUFA by weight is from 1:5 to 1:0.01; and the canned/jarred food product contains at least 50 mg of long-chain PUFA per 13 g serving size of the canned/jarred food product.

12. The composition of claim 11, wherein the antioxidant is selected from the group consisting of:
   a. A sinapyl compound;
   b. A sulfur containing antioxidant;
   c. A ferulic acid containing antioxidant;
   d. Vitamin E;
   e. a tocotrienol; or
   f. curcumin.

13. The composition of claim 12, wherein the sulfur containing antioxidant is isolated from broccoli.

14. The composition of claim 11, further comprising at least one of vegetal chitosan and chitin-glucan at 0.1% to 4.0% by weight of the first oil, wherein the at least one of vegetal chitosan and chitin-glucan is mixed into the first oil prior to being incorporated into the composition.

15. The composition of claim 11, wherein the canned/jarred food product is mayonnaise, or a salad dressing, French dressing, or peanut butter, or nut butter, or pasta sauce.

16. The composition of claim 15, wherein the salad dressing is Ranch or Caesar.

17. A processed food base for producing a finished mayonnaise, comprising the composition of claim 11, an acidifying ingredient, and an egg yolk-containing ingredient; wherein a standard serving portion of the finished mayonnaise contains at least 50 mg of long-chain PUFAs; and the base product comprises at least 65% by weight vegetable oil.

18. A processed food base product for producing a finished salad dressing, comprising the composition of claim 11, an acidifying ingredient, an egg yolk-containing ingredient, and a starchy paste; wherein a standard serving portion of the finished salad dressing contains at least 50 mg of long-chain PUFAs; and the base product contains at least 30% by weight of vegetable oil and at least egg yolk solids equivalent to 4% by weight of liquid egg yolks.

19. A processed food base for producing a finished French dressing, comprising the composition of claim 11 and an acidifying ingredient, wherein a standard serving portion of the finished French dressing contains at least 50 mg of long-chain PUFAs and the base product contains at least 35% by weight of vegetable oil.

* * * * *